(12) United States Patent
Bradley

(10) Patent No.: US 7,549,744 B2
(45) Date of Patent: Jun. 23, 2009

(54) APPARATUS AND METHOD FOR TESTING VISUAL RESPONSE

(75) Inventor: Gordon Bradley, West Yorkshire (GB)

(73) Assignee: Brigantia Software Limited, North Yorkshire (GB)

( * ) Notice: Subject to any disclaimer, the term of this patent is extended or adjusted under 35 U.S.C. 154(b) by 625 days.

(21) Appl. No.: 10/479,723

(22) PCT Filed: May 29, 2002

(86) PCT No.: PCT/GB02/02261

§ 371 (c)(1),
(2), (4) Date: Jul. 9, 2004

(87) PCT Pub. No.: WO02/098289

PCT Pub. Date: Dec. 12, 2002

(65) Prior Publication Data

US 2004/0239878 A1 Dec. 2, 2004

(30) Foreign Application Priority Data

Jun. 5, 2001 (GB) .................................. 0113533.4

(51) Int. Cl.
*A61B 3/10* (2006.01)

(52) U.S. Cl. .................... 351/205; 351/204; 351/211; 351/216

(58) Field of Classification Search ................ 351/211, 351/204, 205, 216, 221, 222, 233, 237, 243
See application file for complete search history.

(56) References Cited

U.S. PATENT DOCUMENTS

| 4,408,616 A | * | 10/1983 | Duffy et al. ................ 600/544 |
| 4,619,505 A | * | 10/1986 | Hache et al. ................ 351/211 |
| 4,846,567 A |   | 7/1989  | Sutter |
| 5,989,194 A | * | 11/1999 | Davenport et al. .......... 600/558 |
| 6,022,107 A |   | 2/2000  | Kutschbach et al. |

FOREIGN PATENT DOCUMENTS

| DE | 199 61 323 A  | 6/2001  |
| WO | WO 99/58046 A | 11/1999 |
| WO | WO 01/39659 A | 6/2001  |
| WO | WO 01/43637 A | 6/2001  |
| WO | WO 01/78586 A | 10/2001 |

\* cited by examiner

*Primary Examiner*—Alicia M Harrington
*Assistant Examiner*—Brandi N Thomas
(74) *Attorney, Agent, or Firm*—Woodard, Emhardt, Moriarty, McNett & Henry LLP

(57) ABSTRACT

Apparatus and method for testing the visual response of a patient is disclosed. The apparatus comprises image generation means (16), image presentation means (12), and detection means (13,14). The image generation means (16) and image presentation means (12) are arranged, in use, to generate and present an image before an eye of the patient at variable predetermined intensity levels. The detection means (13,14) is arranged under the control of a controller (11) to detect a stimulus response to the presented image occurring in the brain of the patient and to display an image of the response of the patient's eye on a monitor (15).

22 Claims, 3 Drawing Sheets

APPARATUS AND METHOD FOR TESTING VISUAL RESPONSE

The present invention relates to apparatus and a method for testing visual response.

BACKGROUND OF THE INVENTION

Medical consultants in the field of ophthalmology often require an indication of the quality of the visual response of various parts of the retina in a patient's eye as this can often provide an indication of the presence or progress of at least three conditions, these being glaucoma, retinitis pigmentosa and, in some cases, multiple sclerosis. All three of these conditions have been known to cause permanent blindness.

Of these three conditions, only glaucoma is at the present time treatable with success. However, early detection of this condition is very important.

One of the earliest symptoms which can be detected is a reduction in the response of the eye to low levels of illumination. Current apparatus to test the field of vision by testing the response of different parts of the retina to low levels of illumination comprises a large, heavy and bulky piece of equipment. A patient is made to sit placing his or her head in a hemispherical screen in a dimly lit room. A light of varying brightness is projected at different points on the screen and the patient is asked to press a button each time a point of light is seen. The responses to the different points of light together with the minimum level of brightness required for detection are stored and printed out on a response map at the end of the test. All, or only selected parts, of the eye may be mapped in this way.

However, the process, which may take fifteen minutes or more, is uncomfortable for the patient and may lead to cramps or stiffness in the neck and back. In addition, only one eye may be tested at a time. The dim lighting required in the room presents problems for patients with poor vision and the need for a physical response can also lead to inaccurate results when testing unreliable patients such as older patients, children or those with very low mental capabilities.

The known apparatus which comprises an expensive and heavy electromechanical device has to be permanently located in one place and requires precise adjustment if the results are to be accurate. In addition, the patient must be reasonably fit physically in order to participate in the test. For example, the test cannot be performed very well for anyone who is unable to sit in one position without serious discomfort for fifteen minutes or more, such as patients suffering with arthritis, slipped discs, wheelchair users or those confined to bed.

Accordingly, it is an object of the present invention to provide apparatus and a method for testing the visual response of a patient in which some or all of the aforementioned disadvantages are at least partly overcome.

SUMMARY OF THE INVENTION

According to a first aspect of the invention, there is provided an apparatus for testing the visual response of a patient, the apparatus comprising image generation means, image presentation means, and detection means, the image generation means and image presentation means being arranged, in use, to generate and present an image before an eye of the patient at variable predetermined intensity levels, and the detection means being arranged, in use, to detect a stimulus response to the presented image occurring in the brain of the patient.

Preferably, the image generation means is arranged, in use, to generate a temporary image at known timings and a predetermined location on the image presentation means and presented at a predetermined intensity level.

Preferably, the image generation means is arranged, in use, to generate a number of images at known timings and at different predetermined locations on the image presentation means and presented at a predetermined intensity level.

Preferably, the image generation means is arranged, in use, to sequentially generate a number of images for presentation at known timings and at different predetermined locations on the image presentation means.

The or each image generated at it's various predetermined locations is preferably arranged, in use, to have it's intensity level varied in a predetermined manner and the detection means is arranged to detect the stimulus response to the variation in intensity level.

Preferably, the sequentially generated images are generated according to either a predetermined sequence, or a random or pseudo-random sequence.

The image generation means is preferably arranged, in use, to generate images of progressively increasing intensity or brightness on the image presentation means.

Preferably, the image presentation means is arranged, in use, to be moveable with respect to an eye of the patient. The image presentation means may be arranged for movement in first, second and third mutually perpendicular directions, which first, second and third directions comprise forwards/backwards, left/right and up/down respectively.

Preferably, detection means comprises a transducer arranged, in use, to detect an electrical impulse or signal produced in the brain of the patient in response to stimulation of the eye of the patient by an image on the image presentation means.

First and second transducers may be provided arranged, in use, to detect an electrical impulse or signal produced in the brain of the patient, in response to visual stimulation of left and right hemispheres of the eyes of the patient, respectively.

The detection means is preferably arranged, in use, to supply the electronic signal to a controller.

The apparatus may include electronic filter means arranged, in use, to filter out noise from the electronic signals from the detection means.

Most preferably, the apparatus is arranged such that, in use, the image generation means generates temporary images at successive different locations on the image presentation means whilst varying the intensity or brightness of the images, and the detection means provides an electronic signal when an image is registered as being detected by the eye of the patient, such that, data corresponding to the minimum intensity or brightness level of images which the stimulus responses indicate are visually detectable at the different locations on the image presentation means may be stored in a memory and/or display.

According to a second aspect of the invention, there is provided apparatus for testing the visual response of a patient, the apparatus comprising image generation and presentation means, arranged, in use, to generate and present an image before an eye of the patient, detection means arranged, in use, to detect a stimulus response to the presented image, occurring in the brain of the patient and a controller, the apparatus being arranged such that, in use, the image generation means generates temporary images at successive different locations on the image presentation means whilst progressively varying the intensity or brightness of the images, and the detection means provides an electronic signal to the controller when an image is detected by the eye of the patient, such that the controller is arranged to store in a memory thereof, and/or to display, data corresponding to the minimum intensity or brightness level of images which the stimulus response indicates are visually detectable at the different locations on the image presentation means.

Preferably, the means to project the or each image to the suitable viewing distance is located, in use, between the image presentation means and an eye of the patient, and may comprise one or more lenses and a mounting member arranged, in use, to mount said one or more lenses substantially in front of an eye of the patient.

Preferably, timing means are provided arranged, in use, to measure a time interval between the presentation of an image on the image presentation means and detection of an electrical stimulus response in the brain of the patient, by the detection means.

Preferably, a headset is provided arranged, in use, to be worn on the head of a patient and carrying the or each image presentation means, the detection means, means to project the image on the image presentation means to a suitable distance and mounting means.

The apparatus preferably further comprises visual display means arranged, in use, to display information about the response of the patient's eye to images at different locations and/or of different intensities or brightnesses on the image presentation means.

Preferably, the visual display means is arranged, in use, to present the information in the form of a map.

According to a third aspect of the invention, there is provided a method of operating apparatus for testing the visual response of a patient, wherein the apparatus comprises image generation and presentation means arranged, in use, to generate and present an image before an eye of the patient, and detection means arranged, in use, to detect a stimulus response to the presented image occurring in the brain of the patient, wherein the method comprises generating a number of images at different locations on the image presentation means and at variable predetermined intensity levels and detecting an electrical impulse or signal produced in the patient's brain in response to stimulation of the patient's eye by the images.

The method may comprise generating temporary images at successive different locations on the image presentation means, whilst progressively varying the intensity or brightness of the images.

The method may comprise measuring a time interval between the presentation of an image on the image presentation means and the detection of an electrical stimulus response to the presented image, in the brain of the patient.

The method preferably comprises the step of generating images of progressively increasing intensity or brightness on the image presentation means.

Preferably, the method comprises the step of detecting an electrical impulse or signal produced in the brain of the patient in response to visual stimulation of left and right hemispheres of the eyes of the patient, respectively.

The method may further comprise the step of producing an electronic signal in response to the detection of an electrical impulse or signal in the brain of the patient.

The method may further comprise the step of filtering the electronic signal to filter out noise from the signal.

Preferably, in a calibration step the normal visual response time of a patient to a visually perceived image is calculated.

Preferably, in the detection step the stimulus response is searched for within a time window approximately centred around the normal visual response time following the presentation of an image on the display screen.

Preferably, signals from the brain not appearing within the time windows of interest are utilised to provide a measure of the background noise and employed to filter out such noise.

Preferably, the step of detecting comprises detecting the electrical impulse or signal produced in the patient's brain in response to stimulation of the patient's eye by the images and providing an electronic signal to the controller when such an image is detected by the eye of the patient.

Preferably, subsequent to said detecting step, the controller carries out the step of storing data corresponding to the intensity of brightness of images detected by the eye at the different locations on the image presentation means.

The method may further comprise displaying the data corresponding to the intensity of brightness of images in a map form.

Preferably, the method further comprises displaying a reference image in the form of a map, said reference image corresponding to a normal or expected response of a healthy patient.

BRIEF DESCRIPTION OF THE DRAWINGS

The invention may be carried into practice in various ways, but an embodiment will now be described by way of example only with reference to the accompanying diagrammatic drawings in which.

DETAILED DESCRIPTION OF THE PREFERRED EMBODIMENTS

Figure 1:
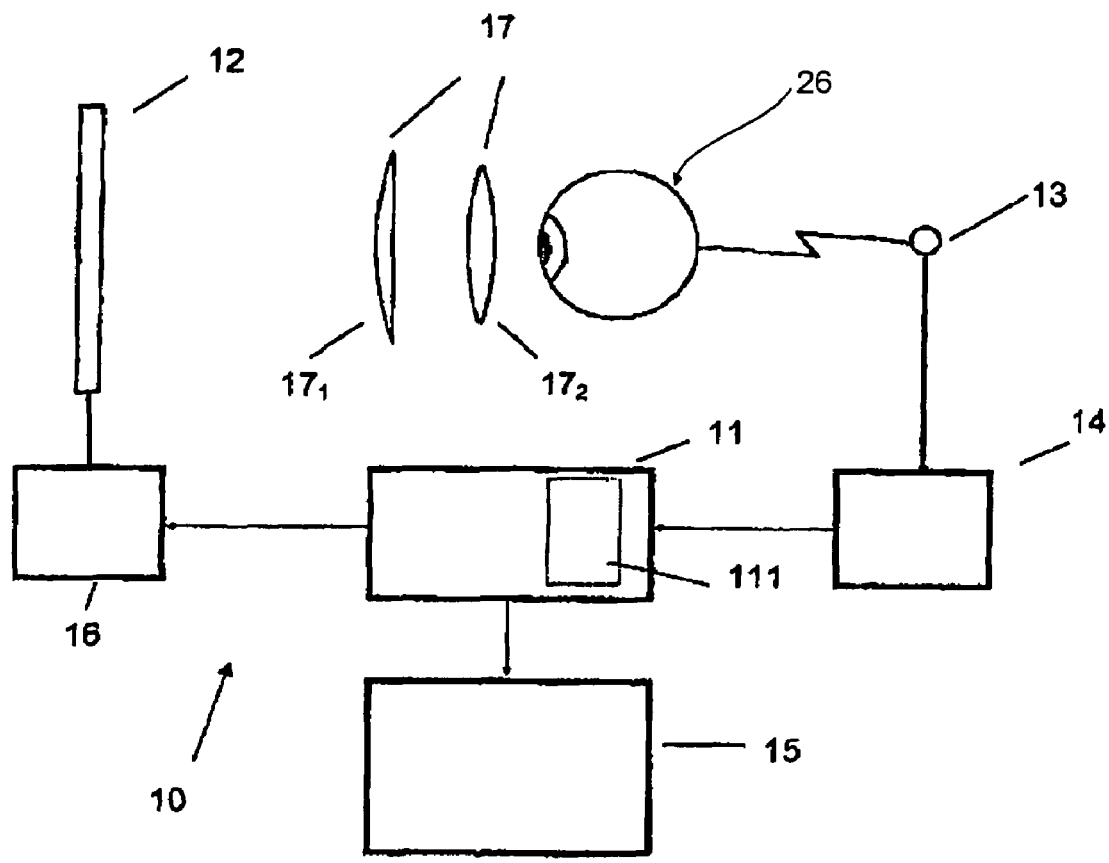
FIG. 1 shows, schematically, apparatus for testing the visual response of a patient according to one embodiment of the present invention.

Referring to FIG. 1 this shows, generally at 10, apparatus for testing the visual response of a patient. The apparatus comprises image generation means, image presentation means, and detection means. In the embodiment shown the image generation means is a function carried out by an electronic controller 11 in conjunction with a display controller 16, the image presentation means is a screen 12, and the detection means comprises a transducer 13 and a A/D converter 14. There is also shown a display monitor 15.

The screen is located in front of a patient's eye represented schematically by 26. Between the eye 26 and the screen 12 is a lens system 17 which is arranged to project images shown on the screen 12 to a suitable distance.

Figure 2:
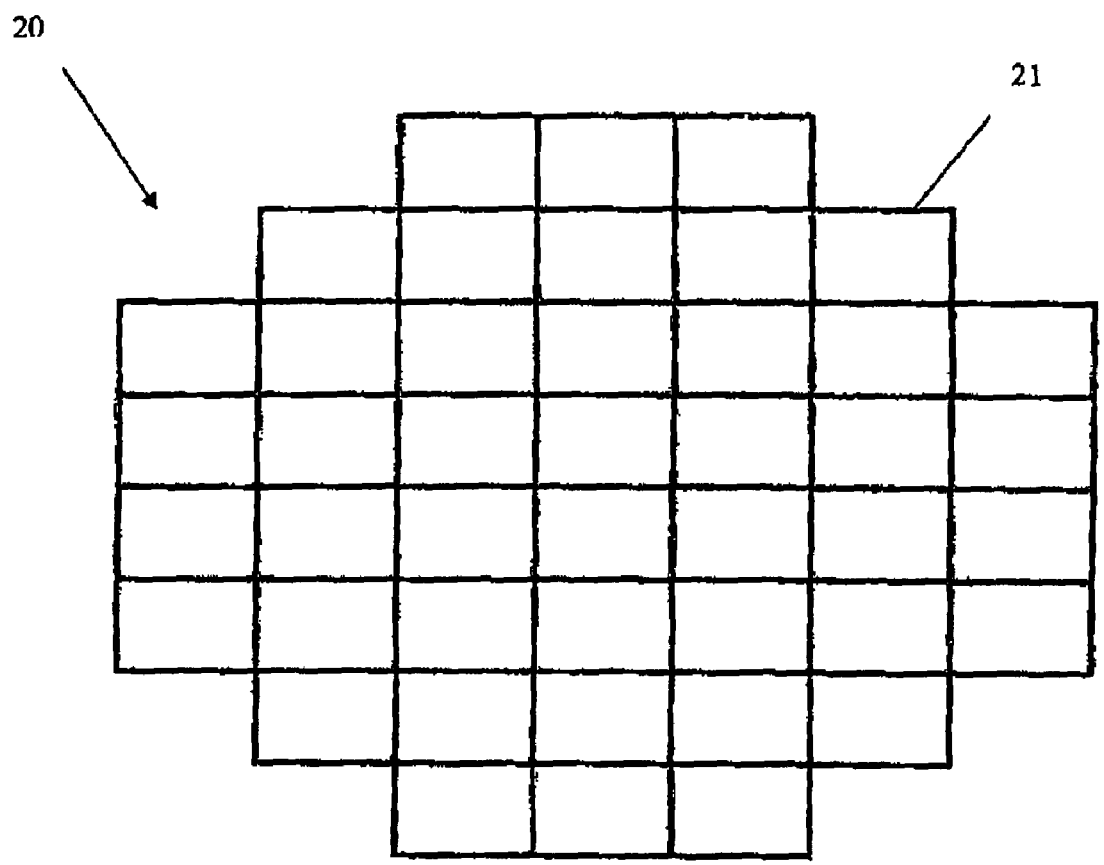
FIG. 2 is a schematic representation of an LED array forming a screen 12 of the apparatus.

Although the screen 12 has been discussed in general terms and may be implemented in a number of ways, the screen in a typical embodiment is composed of LEDs in an array 20 as shown schematically in FIG. 2.

In FIG. 2, the array 20 is composed of a number of sub-arrays 21, each being composed of 5 rows by 7 columns of LEDs. Whilst any visible colour of LED may be used, it has been found that the human eye is most sensitive to visible light somewhere in the area of the visible spectrum between pure red and green (generally at about the green to yellow area). This sensitivity area and how it changes under different light levels is generally known from the "Purkinje Effect". It is preferred to use a light source in this maximum sensitivity area.

In practice, the screen 12 is positioned in front of the eye of the patient under test and the transducer 13 is located on the patient's head and arranged to pick up signals from the part of the patients brain associated with vision. The screen 12, transducer 13 and lens system 17 (including focussing lens $17_1$ and corrective lens $17_2$ [if required]) may be provided together in an integral lightweight headset (not shown) which is worn on the patients head (not shown).

In use, the controller 11 generates electronically an image comprising a point of light which is displayed at a known location, and at a known brightness on the screen 12, which may advantageously comprise a bank of light emitting diodes. If the image is detected on the retina of the patient's eye 26 a nerve stimulus response will occur in the visual cortex of the patient's brain in the form of an electrical signal. The transducer 13 mounted on the patient's head detects the nerve stimulus response and supplies a signal to the controlling computer 11 via a filter (not shown). The purpose of the filter is to filter out any electrical background noise caused by the normal activity of the brain. In practice, filtering may be carried out digitally by the controller 11 and a preferred filtering/processing technique is known as Bayesian analysis.

The controller 11 stores the filtered/processed response from the transducer 13 and displays a representation of the corresponding visual response on the monitor 15 in the form of a dot at a location on the monitor 15 corresponding to a location on the screen 12 at which the point image was displayed to the eye.

In practice, the controller 11 sequentially generates point images on the screen 12 in different locations and the resultant signals from the transducer 13 may be converted into a map, displayed on the monitor, which corresponds to the response of the patient's retina to the images on the screen, thus providing a profile of response of different locations on the retina to visual stimulation.

The map may be printed as a hard copy using a printer (not shown) or may be stored in a memory of the computer for subsequent retrieval or transfer.

A typical procedure for testing a patient's vision using the apparatus shown schematically in FIG. 1 will now be described in detail.

At a first step, a full testing intensity flash is sent to the central area of the eye being tested. Three further flashes of full testing intensity are sent to areas adjacent to the first flash. Timing means is utilised in conjunction with the controller 11 to check for the timing of the maximum brain response in each case. The times between the flash and detection of a brain response are compared to establish the delay between the flash on the screen and the nerve response (commonly known as the P100 time) for the particular patient. In practice, the timing means may be a function of the controller itself, taking advantage of a known frequency of a system clock for instance.

The controller then generates a sequence of points of light on the screen 12 at predetermined steps of intensity and at different locations on the screen according either to a random, pseudo-random or predetermined sequence.

Each time a point of light is displayed on the screen 12, the computer checks whether a nerve response was detected after the expected delay time. The timing of the response for that particular point is compared to the P100 time and the result stored in a memory 111 of the controller 11.

Comparing the delay to the P100 time and knowing the level of brightness of the point of light at that time, the controller 11 is able to create a map of the response profile of the retina, such that each point on the retina is recorded as responding at a particular intensity of light.

In preferred embodiments of the invention, a predetermined or random sequence of points are illuminated on the screen 12 using predetermined steps of increasing brightness at predetermined intervals. By comparing the delay between the timing of the full brightness response (i.e. the P100 time) to the delay time in response to illumination of a particular point, the loss of vision for that point is calculated. Here, if no delay over the P100 time is present for a particular point illuminated at minimum intensity or brightness, then no loss in vision for that point is present.

In an embodiment, a new stimulation is started every 300 msecs. The brightness for the point being analysed is stepped once every 6 msecs for 16 steps, before removing the stimulus. This gives a total stimulus time of 96 msecs within the 300 msec period. If no response is detected in the brain to the minimum brightness stimulus, then at least a 6.25% vision loss is indicated for that point. If no response is detected to the second lowest stimulus, then at least a loss of 12.5% is indicated and so on up to a loss of 100% vision for that point if no response is detected to the 16th (maximum intensity) stimulus for that point. Signals of interest will only occur in a time window centred around the P100 time. Any signals received prior to the P100 time and those received after P100 time plus 96 msecs are considered as background type signals and are used to eliminate background noise effects. It will be appreciated that there are many techniques for noise elimination and that such techniques do not form part of this invention. Here it is sufficient to note that given the knowledge of the P100 response time and the known timing of each brightness pulse, the time of each expected response is known. In this way, a precise inspection of the brain response at the precise expected response time can be made and background noise filtered accordingly.

It is noted here that in using the apparatus, there is no particular observed problem caused by movement of the patient's eyeball during a test run. Image placement occurs rapidly and moves from one part of the screen to another (either using a random or a predetermined sequencing) and the temptation for the patient to move the eyeball during a test sequence is consequently much reduced when compared with other means of testing visual response.

The map shown on the monitor 15 and/or printed as a hard copy, shows characters or dots of different intensities representing the entire surface of the retina, or a part thereof.

The maps may comprise grey scale representations for each point analysed with, for instance, white indicating no vision loss and black a 100% vision loss for a particular point.

Figure 3:
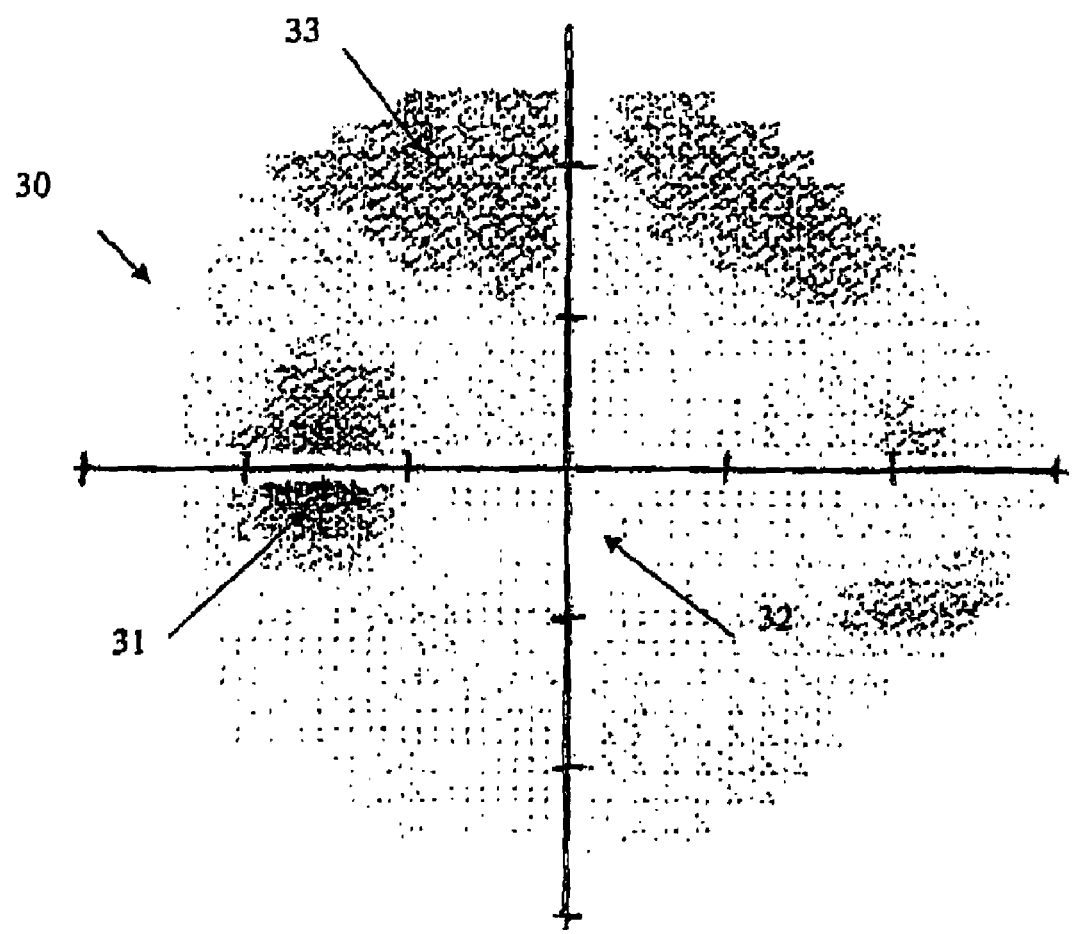
FIG. 3 is an example of an eye "map" of the type which may be produced by the apparatus.

FIG. 3 shows a hard copy print out for a test carried out on the inventor's left eye. The darkest area 31 located to either side of the horizontal axis to the left of the centre of the map 30 represents a blind spot on the retina of the inventors left eye. Light areas such as central area 32 represent areas of good vision, whilst intermediate tones such as the area 33 show degrees of vision impairment.

The complete maps for each eye may be displayed on the monitor 15 and/or printed as a hard copy and may be then stored in the controller memory 111 for subsequent retrieval or transfer.

The number of different levels of intensity for the points of light may be determined by the grey scale representation capabilities of the controller 11 or monitor 15, or indeed by the ability of the screen 12 to output images at different intensity levels. Naturally, the visual response of the eye may be represented on the monitor 15 or a printout in ways other than a grey-scale map. For instance different levels of patient visual response may be represented by different colours, or the "map" might be replaced by a bar-chart representation say.

The test may be performed using monochrome light or may be performed using polychrome light according to requirements and according to the level of sophistication of the apparatus.

The apparatus is essentially portable, since it comprises a lightweight headset and a portable computer. The test may be performed quickly since it is possible to test points every 300 milliseconds.

The screens 12 are preferably movable in three mutually perpendicular axes (forward/back, left/right, up/down) to enable smaller areas of the eye to be scanned in more detail. In this way, if the screen is moved further away from a patient's eye, it will appear smaller to the patient, but will still have the same number of illuminatable points. Movement vertically and/or sideways can then bring the screen to a position in which a corresponding portion of the eye can be examined at an effectively higher resolution.

The use of the headset results in less discomfort for the patient and may be performed in the patient's own home, either standing, sitting or even lying down. Since no manual response is required of the patient, the results of the test are less susceptible to inaccuracies and only a minimum level of training may be required to enable staff to perform the test.

The results of the test, including the determined P100 time and the response profile of the retina thus may enable early detection of several conditions including glaucoma, retinitis pigmentosa and multiple sclerosis.

In particular, it is accepted that the P100 time, which is typically of the order of 95 msecs, remains fairly constant throughout the lives of healthy men, although it may tend to lengthen during the lifetime of women. In persons suffering from multiple sclerosis a significant increase in the P100 time takes place. The apparatus and method described herein may thus provide an early indication of this condition.

Whilst many frequencies of light flashes may be utilised for displaying the images on the screen 12, it is preferred to avoid frequencies between 5 and 30 Hz as it is suggested that light flashes within that frequency range carry a risk of epileptic seizure in some subjects.

It will be understood by those skilled in the art that various modifications may be made to the invention without departing from its scope. In addition, although the apparatus has been described with testing of the visual response of a human patient in mind, it may be suitably adapted for testing the visual response of an animal.

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extend to any novel one, or any novel combination, of the features disclosed in this specification (including any accompanying claims, abstract and drawings), or to any novel one, or any novel combination, of the steps of any method or process so disclosed.

The invention claimed is:

1. Apparatus for testing the visual response of a patient, the apparatus comprising image generation means, image presentation means, and detection means, the image generation means and image presentation means being arranged, in use, to generate and present an image before an eye of the patient at variable predetermined intensity levels, and the detection means being operable, in use, to detect an electrical impulse in the brain of the patient which is a stimulus response to the presented image occurring in the brain of the patient, wherein the image generation means is arranged, in use, to generate images of progressively increasing intensity or brightness on the image presentation means such that a profile of response of different locations in the eye to visual stimulation may be provided.

2. The apparatus of claim 1, wherein the image generation means is arranged, in use, to generate a temporary image at known timings and a predetermined location on the image presentation means and presented at a predetermined intensity level.

3. The apparatus of claim 1, wherein the image generation means is arranged, in use, to generate a number of images at known timings and at different predetermined locations on the image presentation means and presented at a predetermined intensity level.

4. The apparatus of claim 1 wherein, the image generation means is arranged, in use, to sequentially generate a number of images for presentation at known timings and at different predetermined locations on the image presentation means.

5. The apparatus of claim 2, wherein the or each image generated at its various predetermined locations is arranged, in use, to have its intensity level varied in a predetermined manner and the detection means is arranged to detect the stimulus response to the variation in intensity level.

6. The apparatus of claim 4, wherein the sequentially generated images are generated according to either a predetermined sequence, or a random or pseudorandom sequence.

7. The apparatus of claim 1, wherein the image presentation means is arranged to be moveable relative to an eye of the patient in first, second and third mutually perpendicular directions.

8. The apparatus of claim 1, wherein the detection means comprises a first transducer arranged, in use, to detect an electrical impulse or signal produced in the brain of the patient in response to stimulation of the eye of the patient by an image on the image presentation means.

9. The apparatus of claim 8, further comprising a second transducer, wherein the first and second transducers are provided arranged, in use, to detect an electrical impulse or signal produced in the brain of the patient, in response to visual stimulation of left and right hemispheres of the eyes of the patient, respectively.

10. The apparatus of claim 1, wherein the apparatus is arranged such that, in use, the image generation means generates temporary images at successive different locations on the image presentation means whilst varying the intensity or brightness of the images, and the detection means provides an electronic signal when an image is registered as being detected by the eye of the patient, such that, data corresponding to the minimum intensity or brightness level of images which the stimulus response indicate are visually detectable at the different locations on the image presentation means may be stored in a memory and/or display.

11. Apparatus for testing the visual response of a patient, the apparatus comprising image generation and presentation means, arranged, in use, to generate and present an image before an eye of the patient, detection means arranged, in use, to detect a stimulus response to the presented image, occurring in the brain of the patient and a controller, the apparatus being arranged such that, in use, the image generation means generates temporary images at successive different locations on the image presentation means whilst progressively varying the intensity or brightness of the images, and the detection means provides an electronic signal to the controller when an image is detected by the eye of the patient, such that the controller is arranged to store in a memory thereof, and/or to display, data corresponding to the minimum intensity or brightness level of images which the stimulus response indicates are visually detectable at the different locations on the image presentation means, wherein the means to project the or each image to the suitable viewing distance is located, in use, between the image presentation means and an eye of the patient, and may comprise one or more lenses and a mounting member arranged, in use, to mount said one or more lenses substantially in front of an eye of the patient.

12. The apparatus of claim 1, in which timing means are provided arranged, in use, to measure a time interval between the presentation of an image on the image presentation means and detection of an electrical stimulus response in the brain of the patient, by the detection means.

13. The apparatus of claim 1, wherein the apparatus further comprises visual display means arranged, in use, to display information about the response of the patient's eye to images at different locations and/or of different intensities or brightnesses on the image presentation means.

14. A method of operating apparatus for testing the visual response of a patient, wherein the apparatus comprises image generation and presentation means arranged, in use, to generate and present an image before an eye of the patient, and detection means arranged, in use, to detect a stimulus response to the presented image occurring in the brain of the patient, wherein the method comprises generating a number of images at different locations on the image presentation means and at variable predetermined intensity levels and detecting an electrical impulse or signal produced in the patient's brain in response to stimulation of the patient's eye by the images, and wherein the method comprises the step of generating images of progressively increasing intensity or brightness on the image presentation means such that a visual stimulation response profile in respect of different locations in the eye may be generated.

15. The method of claim 14 comprising generating temporary images at successive different locations on the image presentation means, whilst progressively varying the intensity or brightness of the images.

16. The method of claim 14, comprising measuring a time interval between the presentation of an image on the image presentation means and the detection of an electrical stimulus response to the presented image, in the brain of the patient.

17. The method of claim 14, wherein the method comprises the step of detecting an electrical impulse or signal produced in the brain of the patient in response to visual stimulation of left and right hemispheres of the eyes of the patient, respectively.

18. The method of claim 14, wherein in a calibration step the normal visual response time of a patient to a visually perceived image is calculated.

19. The method of claim 18, wherein signals from the brain not appearing within time windows of interest are utilised to provide a measure of the background noise and employed to filter out such noise.

20. The method of claim 14, wherein the step of detecting comprises detecting the electrical impulse or signal produced in the patient's brain in response to stimulation of the patient's eye by the images and providing an electronic signal to the controller when such an image is detected by the eye of the patient.

21. The method of claim 14, further comprising displaying data corresponding to the intensity of brightness of images in a map form.

22. The method of claim 21, wherein the method further comprises displaying a reference image in the form of a map, said reference image corresponding to a normal or expected response of a healthy patient.

* * * * *